(12) United States Patent
Richardson et al.

(10) Patent No.: US 10,324,048 B2
(45) Date of Patent: Jun. 18, 2019

(54) ELECTROMAGNETIC SURFACE RESISTIVITY DETERMINATION

(71) Applicants: Robert E. Richardson, King George, VA (US); Michael B. Slocum, Colonial Beach, VA (US)

(72) Inventors: Robert E. Richardson, King George, VA (US); Michael B. Slocum, Colonial Beach, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 121 days.

(21) Appl. No.: 15/682,783

(22) Filed: Aug. 22, 2017

(65) Prior Publication Data
US 2019/0064081 A1 Feb. 28, 2019

(51) Int. Cl.
*G01N 22/00* (2006.01)
*G01R 29/08* (2006.01)

(52) U.S. Cl.
CPC ......... *G01N 22/00* (2013.01); *G01R 29/0878* (2013.01)

(58) Field of Classification Search
CPC .............................. G01N 22/00; G01R 29/878
See application file for complete search history.

(56) References Cited

U.S. PATENT DOCUMENTS

| 4,733,165 A * | 3/1988 | Richardson | G01R 27/2688 324/601 |
| 2005/0269317 A1 * | 12/2005 | Nguyen | H05B 6/802 219/688 |
| 2008/0276192 A1 * | 11/2008 | Jones | A61C 1/0015 715/772 |
| 2012/0015318 A1 * | 1/2012 | Kasenbacher | A61C 1/0046 433/29 |
| 2015/0011876 A1 * | 1/2015 | Bouton | A61B 5/0507 600/430 |

(Continued)

*Primary Examiner* — Tung X Nguyen
*Assistant Examiner* — Dominic E Hawkins
(74) *Attorney, Agent, or Firm* — Gerhard W. Thielman, Esq.

(57) ABSTRACT

An apparatus is provided for determining an electromagnetic (EM) characteristic of a material, including a chamber, an antenna, a transmitter, a receiver and a processor. The chamber includes a permanent boundary that encloses a volume; a removable panel along the boundary. The panel includes the material. The antenna is disposed in the chamber for transmitting source EM radiation and receiving reflected EM radiation. The transmitter injects the source EM radiation via the antenna into the chamber. The source EM radiation includes continuous wave (CW) and pulse signals. The receiver obtains reverberated EM radiation from the chamber via the antenna and produces an intermediate frequency signal. The processor controls the transmitter and the receiver. The processor determines a decay time of the EM radiation from the intermediate frequency signal. The material is a test substance for comparison with a calibration reference substance on the removable panel having an established EM characteristic in the chamber, based on the decay time for the reference substance. The processor determines the EM characteristic from a decay time of the test substance and a reference decay time of the reference substance.

20 Claims, 4 Drawing Sheets

(56) References Cited

U.S. PATENT DOCUMENTS

| | | | |
|---|---|---|---|
| 2015/0280495 A1* | 10/2015 | Homma | F27D 11/12 |
| | | | 250/492.1 |
| 2016/0178583 A1* | 6/2016 | Ntziachristos | A61B 5/0095 |
| | | | 73/643 |
| 2017/0234943 A1* | 8/2017 | Thielens | G01R 33/12 |
| | | | 324/244 |
| 2018/0058928 A1* | 3/2018 | Banine | G01J 1/4257 |

* cited by examiner

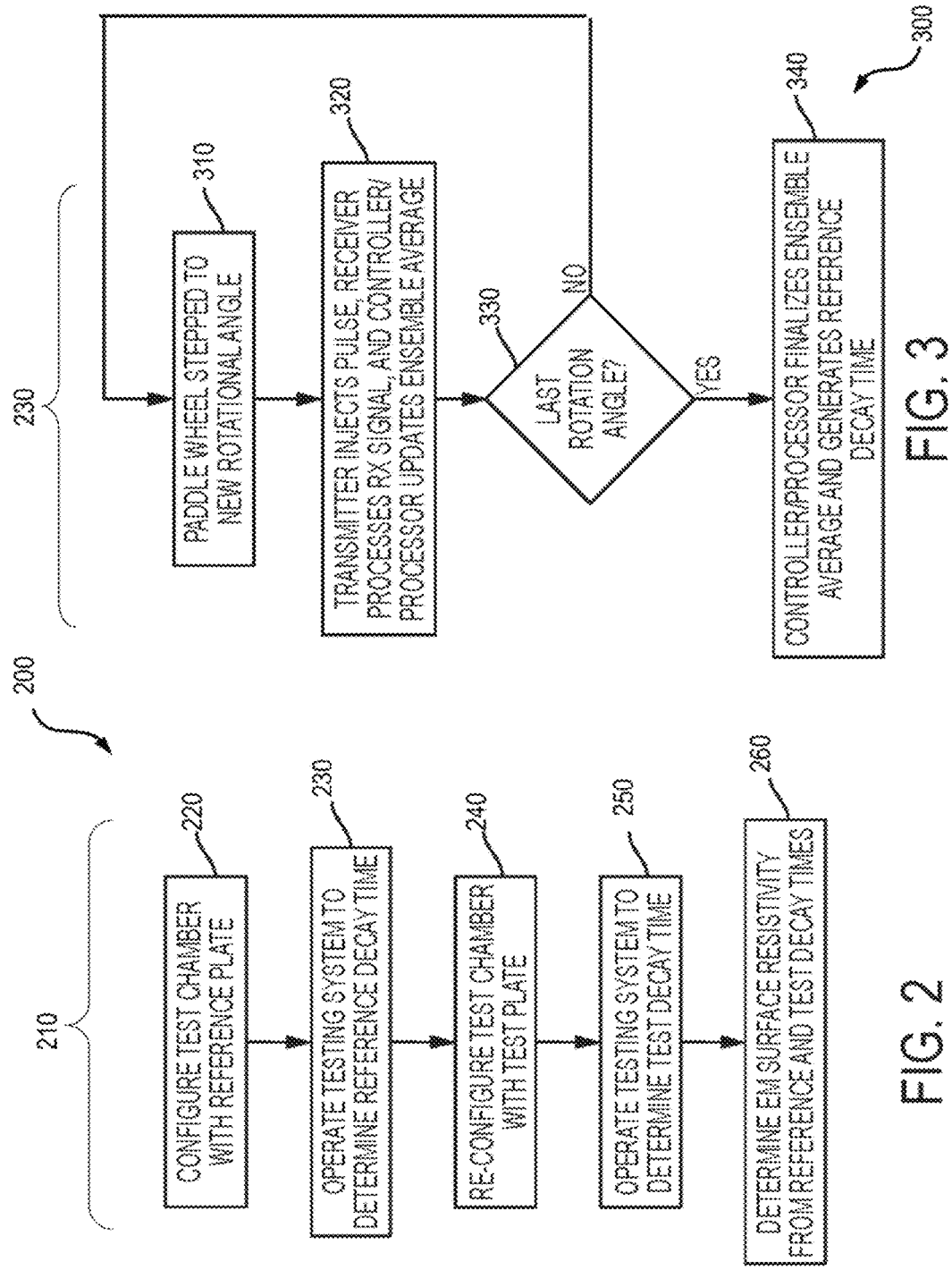

ELECTROMAGNETIC SURFACE RESISTIVITY DETERMINATION

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to techniques for electromagnetic resistance determination within volumetric spaces. In particular, the invention relates to determining surface resistivity of various materials within a chamber, based on comparison with established references.

Statements herein are not to be interpreted as admissions about what is prior art or what is not prior art. Applicants incorporate herein by reference the entire teachings of U.S. Pat. No. 4,733,165. Cavity perturbation measurement on materials with a single-mode cavity is a well-known microwave technique. However, for a large test sample or structure compared against the test frequency wavelength, then the single-mode cavity approach cannot be successfully applied because of difficulties to excite and maintain a single mode in a cavity that is large in terms of wavelength. Further information can be obtained from NSWCDD/TR-081127, "Reverberant Microwave Propagation" by Robert E. Richardson.

SUMMARY

Conventional empirical electrical resistance determination techniques for volumetric spaces yield disadvantages addressed by various exemplary embodiments of the present invention. In particular, exemplary embodiments provide an apparatus for determining an electromagnetic (EM) characteristic of a material, including a chamber, an antenna, a transmitter, a receiver and a processor. The chamber includes a permanent boundary that encloses a volume; a removable panel along the boundary. The panel includes the material. The antenna is disposed in the chamber for transmitting source EM radiation and receiving reflected EM radiation. The transmitter injects the source EM radiation via the antenna into the chamber. The source EM radiation includes continuous wave (CW) and pulse signals.

The receiver obtains the received EM radiation from the chamber via the antenna to produce an intermediate frequency signal. The processor controls the transmitter and the receiver. The processor determines a decay time of the EM energy within the chamber from the intermediate frequency signal. The material is a test substance for comparison with a calibration reference substance on the removable panel having an established EM characteristic in the chamber, based on the decay time for the reference substance. The processor determines the EM characteristic from a test decay time of the test substance and a reference decay time of the reference substance.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. 2 is a high-level flow diagram view for determining the EM surface resistivity of the material;

FIG. 3 is a flow diagram view for determining reference decay time;

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

In accordance with a presently preferred embodiment of the present invention, the components, process steps, and/or data structures may be implemented using various types of operating systems, computing platforms, computer programs, and/or general purpose machines. In addition, those of ordinary skill in the art will readily recognize that devices of a less general purpose nature, such as hardwired devices, or the like, may also be used without departing from the scope and spirit of the inventive concepts disclosed herewith. General purpose machines include devices that execute instruction code. A hardwired device may constitute an application specific integrated circuit (ASIC), a floating point gate array (FPGA), digital signal processor (DSP) or other related component.

In some instances, the behavior or properties of a test structure or material in a reverberant or multi-mode field environment is the quantity of ultimate interest. Because of its sensitivity to small changes in cavity mode Q or 1/e decay time, the technique of ensemble averaging of multi-mode transient decay responses together with equivalent single-mode perturbation calculations enables sensitive measurement of power absorption or loss for material samples or test structures inserted into or within the wall of a multi-mode test chamber.

Figure 1:
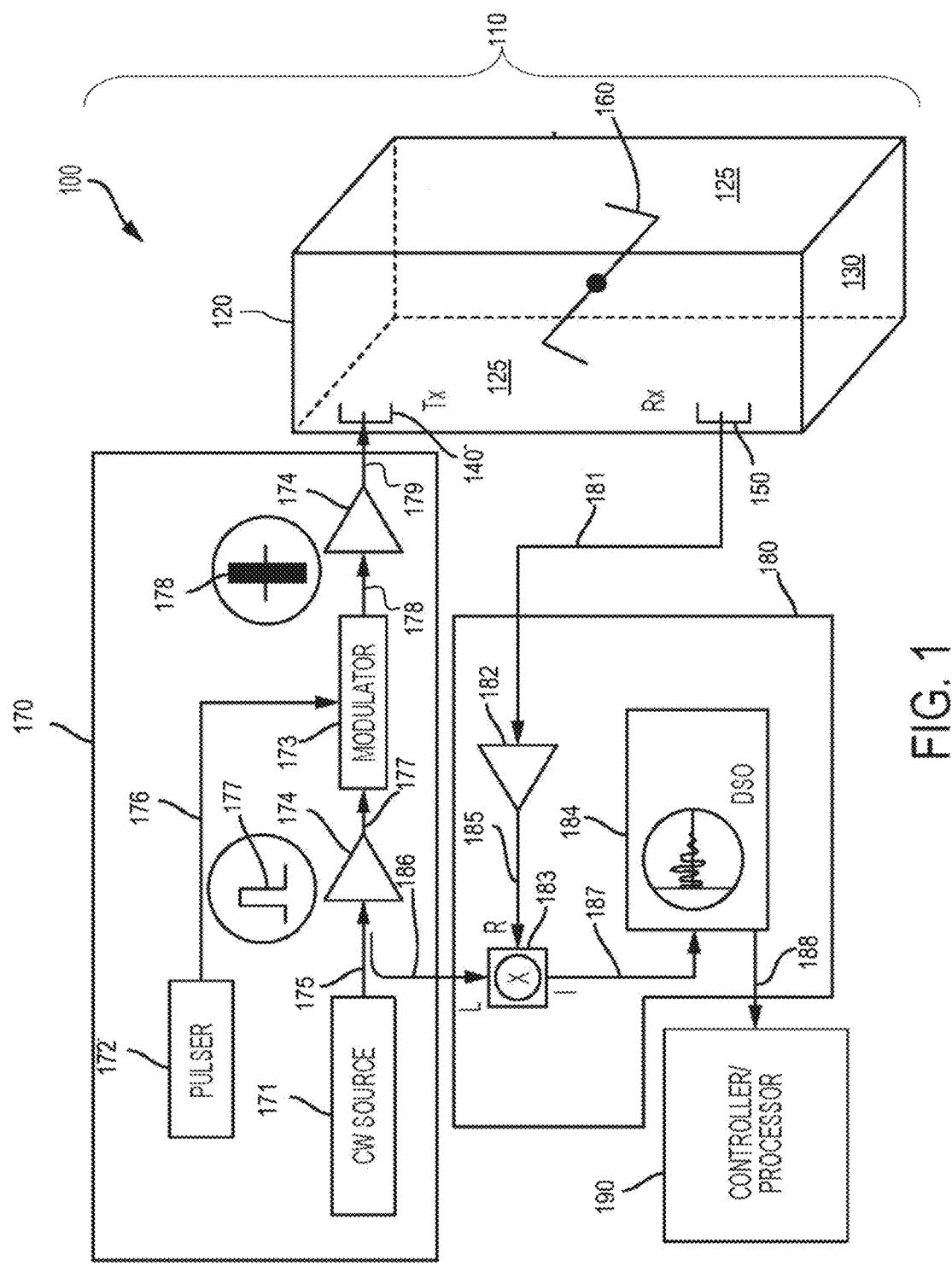
FIG. 1 is a block diagram view of a discrete-pulse system for evaluating electromagnetic (EM) surface resistivity of a material.

FIG. 1 is a block diagram view 100 of an exemplary testing system 110 for determining the electromagnetic (EM) surface resistivity of a test material using a discrete-pulse technique. An enclosure or chamber 120 constitutes an open box comprising a volumetric boundary of rigid walls 125 that house the test or reference material on a removable wall panel 130. The chamber 120 houses a transmit (Tx) antenna 140, a receive (Rx) antenna 150 and a rotatable paddle wheel 160.

A transmitter 170 includes a local oscillator (LO) 171, a pulse generator 172, a modulator 173 and two amplifiers 174. The LO 171 generates a high-frequency continuous-wave (CW) first signal 175. The pulse generator 172 generates a pulse second signal 176 having one discrete pulse minimum. The first amplifier 174 produces an amplified CW third signal 177 from the CW first signal 175. The modulator 173 produces a modulated pulse fourth signal 178 from the received second and third signals 176 and 177. The second amplifier 174 amplifies the modulated pulse fourth signal 178 to deliver a transmit fifth signal 179 to the transmit (Tx) antenna 140.

A receiver 180 receives a sixth signal 181 from the receiver (Rx) antenna 150 in the chamber 120. The receiver 180 includes a low-noise third amplifier 182, a mixer 183 and a digital sampling oscilloscope (DSO) 184. The low-noise amplifier 182 amplifies the sixth signal 181 to produce an amplified continuous wave (CW) received seventh signal 185 (labeled "R"). The mixer 183 receives the seventh signal 185 and an amplified eighth signal 186 from the first amplifier 174 to produce an analog local oscillator ninth signal 187 (labeled "L"). The DSO 184 receives and digitizes the ninth signal 187 to send a digitized intermediate tenth signal 188 (labeled "I") to a control processor 190.

The modulator 173 modulates the amplitude of the amplified CW fourth signal 178 based on each discrete pulse in the pulse second signal 176 to generate the corresponding high-frequency pulse fourth signal 178 amplified by the second amplifier 174 before delivery to the Tx antenna 140. In an example testing scenario, the duration of each pulse fourth signal 178 is about one nanosecond (1 nsec), and the frequency is about 3.0 GHz. Other testing scenarios may employ other pulse durations and/or other pulse frequencies. The control processor 190 can be implemented either as multiple separate devices or else as a single device, such as a personal computer (PC).

The exemplary chamber 120 as shown depicts a bounded volume in a six-sided closed box having five permanent walls 125 that are able to be configured with any one of a plurality of removable sixth-wall panels 130 made of different materials. In one implementation, the five permanent walls 125 are aluminum plates welded together to form a five-sided open box. The chamber 120 can alternatively be a closed box with the wall panel 130 disposed against one of the permanent walls 125. The chamber 120 receives EM radiation from the Tx antenna 140. The walls 125 and panel 130 reflect the EM radiation, and the reverberated signals are received by the Rx antenna 150.

The removable wall panel 130 can be a test plate for surface resistance characterization or a reference plate of established response characteristics. The wall panel 130 as a test plate renders the chamber 120 as a test enclosure. The wall panel 130 as a reference plate renders the chamber 120 as a reference enclosure. A reference plate is made from a suitable material having a known EM surface resistivity, such as (without limitation) aluminum or silver-plated brass. A test plate for the wall panel 130 is composed of the material for which the EM surface resistivity is to be determined. The chamber 120 houses within its volume the Tx antenna 140, the Rx antenna 150, and the rotatable paddle wheel 160.

Under the operation of the control processor 190, the transmitter 170 generates individual EM pulse fifth signals 179 radiated by the Tx antenna 140 into the closed cavity of the chamber 120. The receiver 180 processes the resulting first signals 181 obtained from the Rx antenna 150 in response to reverberant EM signals within the chamber's cavity that are generated by each of the radiated EM pulses. The control processor 190 also controls the angular orientation of the paddle wheel 160.

Receiver 180 includes a low-noise (LN) third amplifier 182, the mixer 183, and the DSO 184. The LN amplifier 182 amplifies the reflected sixth signal 181 received from the Rx antenna 150. The mixer 183 multiplies the amplified seventh signal 185 with the CW eighth signal 186 tapped from the CW signal 175 to generate an analog intermediate frequency (IF) ninth signal 187. The DSO 184 receives the ninth signal 187 and converts instantaneous values of the analog IF ninth signal 187 into digitized values of the digitized IF tenth signal 188. The control processor 190 squares the digitized IF tenth signal 188 and incorporates the squared values into an ensemble averaging process 320 (in FIG. 3) to determine the 1/e decay time of the response of the chamber 120.

The Rx antenna 150 function could be accomplished with individual E- or H-field probes which, by their design, respond to only one component (i.e., E (electric) or H (magnetic), respectively) of the electromagnetic field present in the chamber following the injection of a pulse from the Tx antenna 140. In any case, the analog IF ninth signal 187 going into the DSO 184 represents a field-response signal. The instantaneous values of the analog IF ninth signal 187 are digitized by the DSO 184 and squared by the control processor 190. This yields an ensemble averaging process performed on power values ($E^2$ and/or $H^2$) rather than on field values (E and/or H).

FIG. 2 is a flowchart view 200 of high-level flow diagram of a technique for determining the EM surface resistivity of a test material using the testing system 110 of FIG. 1. In operation 220, the chamber 120 is configured as a reference enclosure with a reference plate made of a calibrated material having an established EM surface resistivity as the sixth wall panel 130. In operation 230, the processor 190 operates the transmitter 170, the receiver 180, and the paddle wheel 160 to generate raw data for determining a reference decay time r, associated with the chamber 120 when configured as a reference enclosure with the reference plate. The processing of operation 230 is described in further detail below with regard to FIG. 3.

In operation 240, the reference plate is removed as the wall panel 130, and the chamber 120 is reconfigured as a test enclosure with a test plate composed of a test material whose EM surface resistivity is to be determined as the wall panel 130. In operation 250, the processor 190 operates the transmitter 170, the receiver 180, and the paddle wheel 160 to generate raw data for determining a test decay time $\tau_T$ associated with the chamber 120 when configured with the test plate. The processing of operation 250 is analogous to the processing of operation 230, as described in further detail below with regard to FIG. 3.

In operation 260, the EM surface resistivity $R_T$ of the test material is determined according to eqn. (1) as follows:

$$R_T = R_R + \Delta R, \quad (1)$$

where $R_R$ is the known EM surface resistivity of the reference material, and $\Delta R$ is the difference in EM surface resistivity between the reference material and the test material. The resistivity difference $\Delta R$ is provided by eqn. (2) as follows:

$$\Delta R = \frac{\Delta(1/\tau)3\mu_0 V}{4S}, \quad (2)$$

where the constant $\mu_0$ is the known magnetic permeability of space, V is the interior volume of the chamber 120 (effectively serving as the reference enclosure), S is the surface area of the wall panel 130 (which is the same for the reference panel and the test panel), and $\Delta(1/\tau)$ is the difference between the inverse of the reference decay time $\tau_R$ and the inverse of the test decay time $\phi_T$, as given by eqn. (3) as follows:

$$\Delta\left(\frac{1}{\tau}\right) = \frac{1}{\tau_T} - \frac{1}{\tau_R}. \tag{3}$$

As indicated by eqn. (2), the resistivity difference $\Delta R$ is directly proportional to the inverse decay time difference $\Delta(1/\tau)$ and the chamber volume V and inversely proportional to the sixth-wall surface area S. The 1/e reference decay time $\tau_r$ may be calculated using eqn. (4) as follows:

$$\tau_R = \frac{4.3429}{R_D(\text{dB}/\mu \text{ sec})}, \tag{4}$$

where decay rate $R_D$ is the slope of trend line 470 in FIG. 4 (described below) in dB/μsec, and numerator 4.3429 is 10·log(e).

The processor 190 automatically performs at least some of the data processing to determine the reference decay time $\tau_R$ in operation 250, the test decay time $\tau_T$ in operation 250, and the test material EM surface resistivity $R_T$ in operation 260. The injection of a single short-duration high-frequency pulse second signal 176 results in time-dependent reverberant reflected sixth signal 181 within the cavity of chamber 120 such that the EM field within the cavity has time-varying amplitude peaks and valleys at different locations within that cavity's volume V.

The precise locations of those amplitude peaks and valleys depend on the physical characteristics of the chamber 120 including the physical characteristics of the Tx and Rx antennas 140 and 150 and the paddle wheel 160. According to preferred embodiments, the paddle wheel 160 is stepped to different rotational angles during operations 230 and 250 in order to mix the EM modes such that the amplitude peaks and valleys shift to different locations in response to distinct rotational angles of the paddle wheel 160.

FIG. 3 is a flowchart view 300 of the processing diagram implemented during operation 230 of FIG. 2 using the testing system 110 to determine the reference decay time $\tau_R$ associated with the chamber 120 using a reference panel for the wall panel 130. The processing of FIG. 3 is analogous to the processing implemented during operation 250 using the testing system 110 to determine the test decay time $\tau_T$ associated with the chamber 120.

In operation 310, the control processor 190 steps the paddle wheel 160 to a new rotational angle. In operation 320, the processor 190 causes the transmitter 170 to inject a single, short-duration high-frequency pulse fifth signal 179 into the chamber 120, the receiver 180 processes the resulting sixth signal 181 to generate the digitized IF tenth signal 188 for that rotational angle, and the processor 190 squares and stores the digitized IF tenth signal 188 to update the ensemble average. Operation 330 causes processing to return for repeating operations 310 and 320 for the next rotational angle until all of the distinct rotational angles have been employed. In operation 340, the processor 190 finalizes the ensemble average for all of the different rotational angles to generate a dataset, from which a value for the reference decay time $\tau_r$ of the reference enclosure is derived.

During each implementation of operation 320, the paddle wheel 160 has a different orientation, and a short pulse fifth signal 179 excites the chamber 120 with microwave energy. Operation 340 performs analysis on ensemble-averaged transient-squared chamber E- and/or H-field responses from the Rx antenna 150 within the chamber 120. Because the chamber 120 is very large compared with wavelength dimensions, pulsed excitation produces many different cavity modes, each of a slightly different frequency. Modes beat together as they decay producing a non-monotonic but ultimately decaying response. Ensemble averaging removes the beating effects, thereby uncovering the essential exponential-decay feature of the modes. The ensemble-averaged transient-squared field response is a mean squared average (versus time), being proportional to EM energy present in the chamber 120 following excitation.

Figure 4:
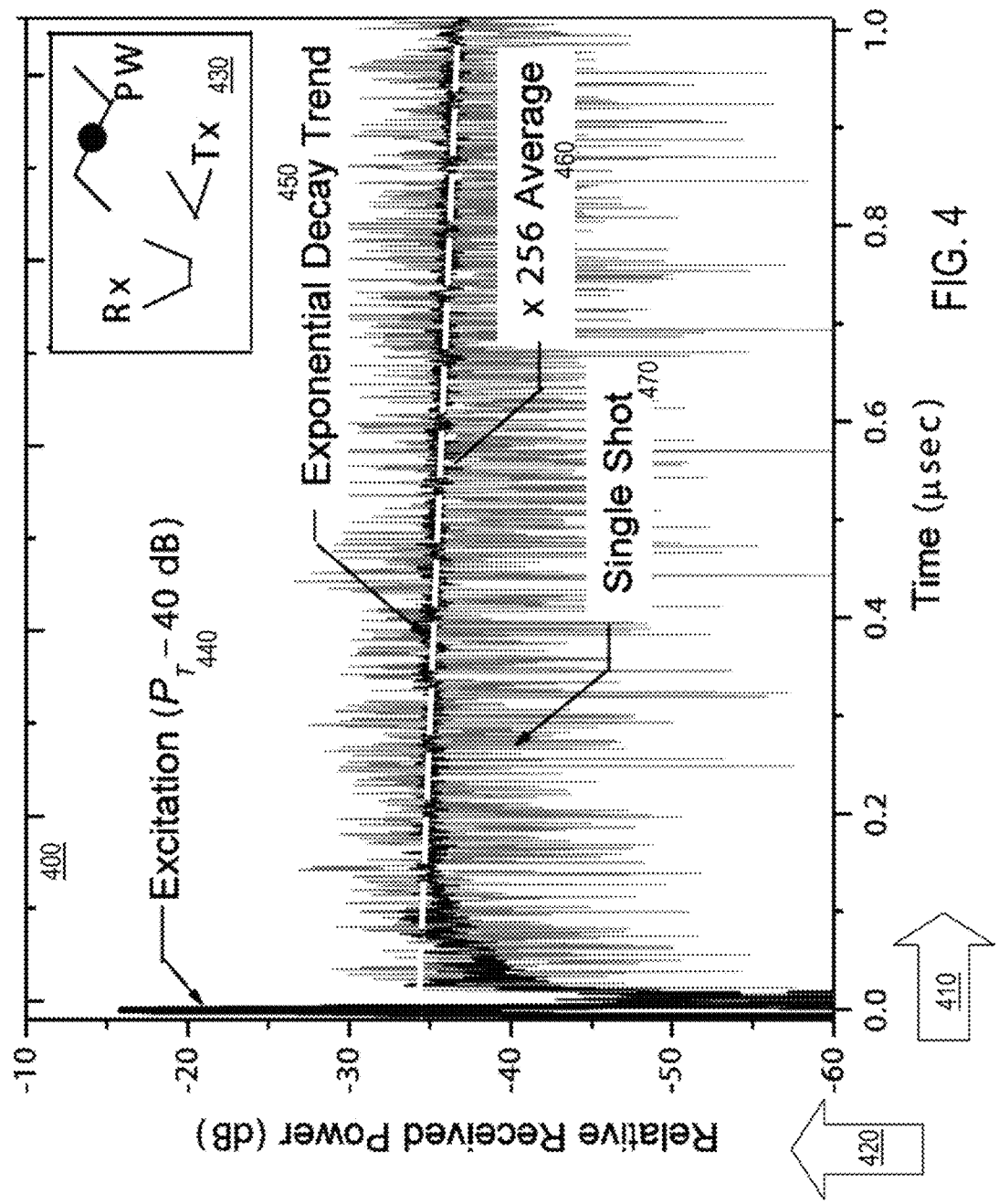
FIG. 4 is a graphical view of select representative data.

FIG. 4 is a graphical representation view 400 of some of the data generated during the processing operation 230. The abscissa 410 denotes time in microseconds (μsec), while the ordinate 420 denotes relative received power in decibels (dB). A legend 430 depicts antenna configuration within the chamber 120. The graphical view 400 depicts an excitation peak 440, an exponential decay trend 450, averaged response 460, and single shot response 470. In particular, the single shot response 470 for the Rx sixth signal 181 shows response to an EM pulse fifth signal 179 injected into the chamber 120 for a particular angular orientation of the paddle wheel 160. The response 470 shows instantaneous received (Rx) power derived by squaring the IF tenth signal 188, and represents raw data generated during operation 230.

View 400 also shows average response 460 representing the ensemble averaged relative Rx power of the received sixth signal 181 as a function of time 410 for 256 different injected EM pulse fifth signals 179 at 256 different angular orientations of the paddle wheel 160. As shown in FIG. 4, the averaged relative Rx power 460 demonstrates an exponential decay trend 450. The reference decay time $\tau_R$ derives from the slope of that exponential decay trend 450 and can be defined as the time required for the averaged relative Rx power to decrease by a factor equal to the transcendental constant e (about 2.71828) from its peak excitation value, soon after injection of the EM pulse fifth signal 179 into the chamber 120. Other suitable implementations are also possible. In any case, the same definition of decay time for determining the reference decay time $\tau_R$ can also be used to determine the test decay time $\tau_T$ during the analogous processing of operation 250 for the chamber 120.

Those skilled in the art will understand that the discrete-pulse techniques of FIGS. 1 through 4 are merely example embodiments for determining the EM surface resistivity of a test material. Other techniques include synthetic time-domain (TD) techniques in which an EM emitter injects a swept-frequency CW signal into the chamber 120 and then, using fast Fourier transform (FFT)-based processing on the resulting chamber response, a network analyzer as the processor 190 determines the chamber response to a pulsed signal.

Figure 5:
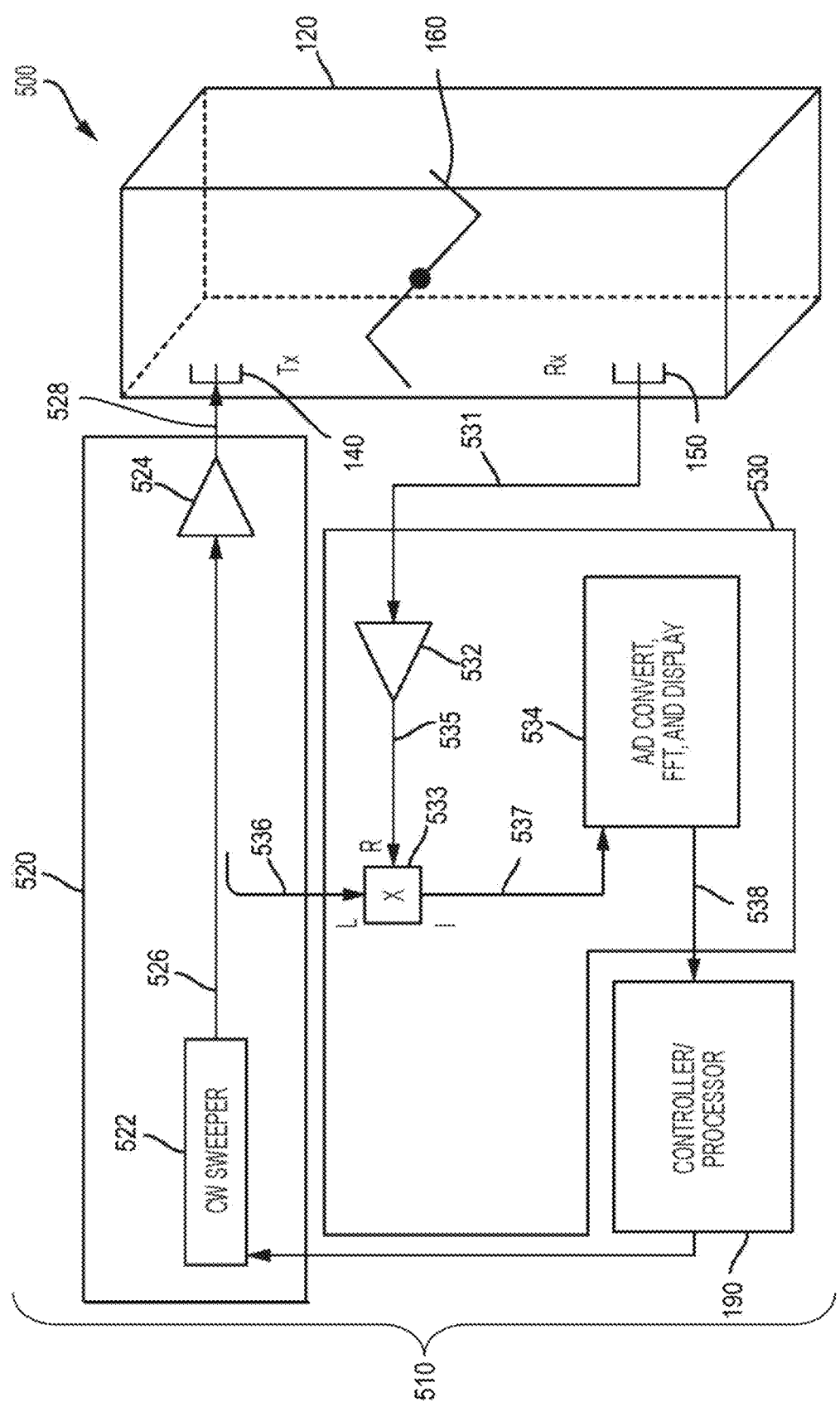
FIG. 5 is a block diagram view of a homodyne synthetic time-domain system for determining the EM surface resistivity of the test material.

FIG. 5 is a simplified block diagram view 500 of a homodyne testing system 510 according to an alternative embodiment that employs a synthetic TD technique for the chamber 120. The system 510 includes a transmitter 520 with a CW sweeper 522 and a fourth amplifier 524. The sweeper 522 generates a swept CW eleventh signal 526 at a frequency selected by the control processor 190. The fourth amplifier 524 amplifies the swept CW eleventh signal 526 and applies the resulting amplified swept CW twelfth signal 528 to the Tx antenna 140 in the chamber 120. Testing system 510 further includes a receiver 530 and the processor 190. The Rx antenna 150 provides a received thirteenth signal 531 from the chamber 120 responsive to reverberated EM energy from the transmitter 520 provided to the Tx antenna 140. The receiver 530 includes an LN amplifier 532, a mixer 533, and an FFT processor 534.

The LN amplifier 532 amplifies the Rx thirteenth signal 531 received from the Rx antenna 150 in the chamber 120, and the mixer 533 combines the resulting amplified Rx fourteenth signal 535 with a swept CW fifteenth signal 536 tapped from the CW eleventh signal 526 to generate the IF sixteenth signal 537. The FFT processor 534 digitizes and applies FFT-based processing to the analog IF sixteenth signal 537 to generate an equivalent digital IF seventeenth signal 538 of the chamber response to pulsed excitation. Alternatively, the equivalent digital IF seventeenth signal 538 could also be derived within the processor 190 by digitizing and Fourier transforming the analog IF sixteenth signal 537. In any case the processor 190 squares the seventeenth signal 538 and incorporates the squared value into the ensemble averaging process 320 to determine the 1/e decay time of the response of the chamber 120.

The ensemble averaging process is performed on signals proportional to received power, which is proportional to the square of E and/or of H (i.e., $E^2$ and/or $H^2$). The IF signals 537 and 538, as well as ninth and tenth IF signals 187 and 188 in the direct pulsed system are proportional to E and/or H. Thus, digital IF seventeenth signal 538 is squared immediately before being fed into the ensemble averaging process in the processor 190. IF tenth signal 188 is analogous to seventeenth signal 538, with the only difference being that the latter is synthesized from a swept CW excitation signal by FFT processing. Both signals 188 and 538 represent chamber transient E and/or H field responses to a pulsed microwave signal. The ensemble averaging process by processor 190 is identical in views 100 and 500.

Artisans of ordinary skill will recognize that there are other testing systems that can be used to perform alternative synthetic TD techniques to determine the EM surface resistivity of a test material, including, for example, heterodyne receiver-based testing systems having two swept-CW oscillators—particularly one for generating the injected pulses and another used as a local oscillator in a receiver for measuring chamber response. In general, synthetic TD techniques can be implemented using commercially available vector network analyzers that provide the relevant sweepers, mixers, amplifiers, analog-to-digital converters, and digital signal processors that perform FFT functions. Squaring and ensemble averaging functions could be performed separately in a PC-based processor 190.

Those skilled in the art will understand that any real-world testing systems will have various, associated EM losses that impact the raw data generated during the individual testing procedures for the reference and chamber 120s. Because the overall technique is based on relative measurements of the reference as the wall panel 130 and the chamber 120 using otherwise substantially identical testing systems, the assumption is that the two sets of EM losses will be substantially identical and therefore irrelevant to the determination of the EM surface resistivity of the test material. In particular, other than those related to the different EM surface resistivities of the reference and test materials, the effects of the EM losses for the two phases of testing are assumed to cancel each other out when the inverse-decay-time difference $\Delta(1/\tau)$ of eqn. (3) is determined.

Although exemplary embodiments have been described in the context of box-shaped testing chambers in which the reference and test plates correspond to the sixth wall of the testing chamber, the claims are not so limited. In general, the reference and test plates for the wall panel 130 may correspond to portions of the chamber 120 that are smaller than an entire wall or larger than a single wall. Furthermore, testing chambers having shapes other than rectilinear prisms are also possible.

Exemplary embodiments have been described in the context of testing chambers having the Tx antenna 140 and the Rx antenna 150 as distinct components. Alternatively, the chamber 120 may employ a single antenna employed to inject EM pulses and provide the resulting Rx signals. In that case, the transceiver circuitry outside of the testing chamber can include a circulator or other directional coupler to forward the outgoing and incoming signals in the appropriate directions.

Although exemplary embodiments have been described in the context of determining the EM surface resistivity of materials, the claims are not so limited. Note that loss-related properties may also be considered as power-capture properties. The ensemble averaging technique together with the over-moded cavity perturbation calculations as applied for determining surface resistivity may be applied more generally to determine other loss-related properties, such as a power capture or power loss area $A_{loss}$. These properties can be obtained for a material sample, an absorptive structure or calibration structure such as an antenna, or other test structure inserted into a chamber 120 or in a permanent wall 125.

The loss area $A_{loss}$ of the sample or structure is calculated according to eqn. (5) as follows:

$$A_{loss} = \frac{\Delta(1/\tau) \cdot V}{c}, \quad (5)$$

where $\Delta(1/\tau)$ is the inverse-decay-time difference of eqn. (3), V is the interior volume of the test chamber, and c is the speed of light. Surface resistivity is one technique for specifying loss characteristics of a material or structure. In other contexts, the loss properties of a material or structure may simply be represented by a power loss or power capture area. In such a case, the product of power density (watt/m²) in the test chamber 120, or in a chamber where the material or structure is ultimately employed, and loss area $A_{loss}$ (m²) represents power (watts) lost, captured or otherwise removed from the reverberant EM field within that chamber.

Select embodiments provide a test or calibration system 110 for determining an EM characteristic of a test material. The system 110 includes the chamber 120, the transmitter 170, the receiver 180 and the control processor 190. The chamber 120 is configurable as either a reference enclosure with the wall panel 130 constituting a reference material having a known reference-material EM characteristic, or a test enclosure with the wall panel 130 comprising the test material. The processor 190 controls operations of the system 110. The transmitter 170 injects EM energy as the fifth signal 179 into the chamber 120 as a reference or test enclosure, and the receiver 180 processes the received sixth signal 181 from the chamber 120 to generate data for determining a reference or test decay time of the chamber 120.

The EM characteristics of the established reference material, as well as the reference and test decay times determine the EM characteristic of the panel material for the wall panel 130. In various embodiments, the transmitter 170 injects the EM energy into the chamber 120 as a first instance of an EM pulse, and the transmitter 170 injects the EM energy into the chamber 120 as a second instance of the EM pulse.

In select embodiments, the transmitter 520 injects the EM energy into the chamber 120 as a swept-frequency CW twelfth signal 528. The decay time is thereby determined from corresponding synthesized pulse data, and the transmitter 520 is adapted to inject the EM energy into the chamber 120 as an alternative equivalent swept-frequency CW signal. The decay time can be determined based on corresponding synthesized pulse data. In exemplary embodiments, the transmitter 170 injects the EM energy as the fifth signal 179 into the chamber 120 using the Tx antenna 140, and the receiver 180 processes the received sixth signal 181 received from the Rx antenna 150.

In exemplary embodiments, the chamber 120 is a six-sided box having one wall panel 130 composed either of the reference material or the test material, and the remaining five sides 125 remain identical for both test and reference operations. The exemplary chamber 120 can include a rotatable paddle wheel 160. The control processor 190 rotates the paddle wheel 160 in a plurality of distinct rotational orientations to generate the decay time for either reference or test operations. In select embodiments, the processor 190 generates ensemble-averaged relative received power 460 as a function of time for the chamber 120.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. An apparatus for determining an electromagnetic (EM) characteristic of a material, said apparatus comprising:
    a chamber including a permanent boundary that encloses a volume;
    a removable panel along said boundary, said panel including the material;
    an antenna disposed in said chamber for transmitting source EM radiation and receiving reflected EM radiation;
    a transmitter for injecting said source EM radiation via said antenna into said chamber, said source EM radiation including continuous wave (CW) and pulse signals;
    a receiver for obtaining said reflected EM radiation from said chamber via said antenna, said receiver producing an intermediate frequency signal; and
    a processor for controlling said transmitter and said receiver, and for determining a decay time between said source and reflected EM radiation from said intermediate frequency signal, wherein
    the material is a test substance for comparison with a calibration reference substance on said removable panel having an established EM characteristic in said chamber, based on said decay time for said reference substance,
    said processor determines the EM characteristic from a test decay time of said test substance and a reference decay time of said reference substance, and
    said transmitter further includes:
        a CW oscillator for generating said CW signal,
        a pulse generator for generating a pulse signal, and
        a modulator for combining said CW and pulse signals as said source EM radiation.

2. The apparatus according to claim 1, further comprising:
    a paddle wheel disposed in said chamber for reflecting said source EM radiation therein, said paddle wheel being configurable in an orientation of a plurality of orientations.

3. The apparatus according to claim 2, wherein said orientation of said paddle wheel is controllable by said processor.

4. The apparatus according to claim 1, wherein said antenna comprises a receiver antenna for obtaining said reflected EM radiation, and a transmitter antenna for injecting said source EM radiation.

5. The apparatus according to claim 1, wherein said transmitter further comprises an amplifier for amplifying said CW and pulse signals.

6. The apparatus according to claim 1, wherein said transmitter further comprises:
    a CW sweeper for generating said CW and pulse signals as said source EM radiation.

7. The apparatus according to claim 6, wherein said transmitter further comprises an amplifier for amplifying said CW and pulse signals.

8. The apparatus according to claim 1, wherein said receiver further comprises:
    a mixer for combining reflected EM radiation from said antenna and said CW signal from said transmitter to produce an integrated signal; and
    an analog-to-digital fast Fourier transform converter for producing an intermediate frequency signal for said processor to determine said decay time.

9. The apparatus according to claim 8, wherein said receiver further comprises an amplifier for amplifying reflected EM radiation.

10. The apparatus according to claim 1, wherein said permanent boundary includes an opening that said removable panel closes.

11. The apparatus according to claim 1, wherein the EM characteristic is surface resistivity determined by inverse decay time difference that subtracts inverse of said test decay time from inverse of said reference decay time.

12. The method according to claim 11, wherein the EM characteristic is surface resistivity determined by inverse decay time difference that subtracts inverse of said test decay time from inverse of said reference decay time.

13. An apparatus for determining an electromagnetic (EM) characteristic of a material, said apparatus comprising:
    a chamber including a permanent boundary that encloses a volume;
    a removable panel along said boundary, said panel including the material;
    an antenna disposed in said chamber for transmitting source EM radiation and receiving reflected EM radiation;
    a transmitter for injecting said source EM radiation via said antenna into said chamber, said source EM radiation including continuous wave (CW) and pulse signals;
    a receiver for obtaining said reflected EM radiation from said chamber via said antenna, said receiver producing an intermediate frequency signal; and
    a processor for controlling said transmitter and said receiver, and for determining a decay time between said source and reflected EM radiation from said intermediate frequency signal, wherein the material is a test substance for comparison with a calibration reference substance on said removable panel having an established EM characteristic in said chamber, based on said decay time for said reference substance, said processor determines the EM characteristic from a test decay time of said test substance and a reference decay time of said reference substance, and said receiver further comprises:
a mixer for combining reflected EM radiation from said antenna and said CW signal from said transmitter to produce an integrated signal; and
a digital sampling oscilloscope for producing said intermediate frequency signal for said processor to determine said decay time.

14. The apparatus according to claim 13, wherein said receiver further comprises an amplifier for amplifying reflected EM radiation.

15. The apparatus according to claim 13, wherein said receiver further comprises:
a mixer for combining reflected EM radiation from said antenna and said CW signal from said transmitter to produce an integrated signal; and
an analog-to-digital fast Fourier transform converter for producing an intermediate frequency signal for said processor to determine said decay time.

16. The apparatus according to claim 15, wherein said receiver further comprises an amplifier for amplifying reflected EM radiation.

17. A computer-implemented characterization method for determining an electromagnetic (EM) characteristic of a material, said method comprising:
enclosing a volume in a chamber with a permanent boundary;
disposing the material on a removable panel along said boundary that further includes incorporating a reference substance as the material for determining a reference characteristic and separately incorporating a test substance as the material for determining a test characteristic;
disposing an antenna in said chamber for transmitting source EM radiation and receiving reflected EM radiation;
connecting a transmitter for injecting source EM radiation to said antenna into said chamber, said source EM radiation including continuous wave (CW) and pulse signals;
connecting a receiver to said antenna, said receiver obtaining said reflected EM radiation from said chamber via said antenna and producing an intermediate frequency signal;
controlling said transmitter and said receiver by a processor; and
determining a decay time between said source and reflected EM radiation from said intermediate frequency signal by said processor;
comparing the material as a test substance with a calibration reference substance on said removable panel having an established EM characteristic in said chamber, based on said decay time for said reference substance, and
determining the EM characteristic from a test decay time of said test substance and a reference decay time of said reference substance by said processor.

18. The method according to claim 17, wherein disposing said antenna further comprises disposing a receiver antenna for obtaining said reflected EM radiation from said chamber and a transmitter antenna for injecting said source EM radiation into said chamber.

19. The method according to claim 17, further comprising:
disposing a paddle wheel in said chamber for reflecting said source EM radiation therein, said paddle wheel being configurable in an orientation of a plurality of orientations.

20. The method according to claim 19, further comprising:
controlling said orientation of said paddle wheel by said processor.

* * * * *